(12) United States Patent
Murakami et al.

(10) Patent No.: US 8,258,165 B2
(45) Date of Patent: *Sep. 4, 2012

(54) PHARMACEUTICAL COMPOSITION

(75) Inventors: Yasushi Murakami, Yokohama (JP);
Naoko Kobayashi, Yokohama (JP);
Azuma Nishio, Yokohama (JP); Nobuo Kubota, Yokohama (JP)

(73) Assignee: Pola Pharma Inc., Tokyo (JP)

( * ) Notice: Subject to any disclaimer, the term of this patent is extended or adjusted under 35 U.S.C. 154(b) by 134 days.

This patent is subject to a terminal disclaimer.

(21) Appl. No.: 12/598,044

(22) PCT Filed: Apr. 16, 2008

(86) PCT No.: PCT/JP2008/000994
§ 371 (c)(1),
(2), (4) Date: Oct. 29, 2009

(87) PCT Pub. No.: WO2008/152764
PCT Pub. Date: Dec. 18, 2008

(65) Prior Publication Data
US 2010/0130576 A1 May 27, 2010

(30) Foreign Application Priority Data
Jun. 14, 2007 (JP) ................. 2007-156980

(51) Int. Cl.
*A01N 43/52* (2006.01)
*A61K 31/415* (2006.01)
*C07D 233/28* (2006.01)
*C07D 233/91* (2006.01)

(52) U.S. Cl. ..................................... 514/398

(58) Field of Classification Search .............. 514/398; 548/327.5
See application file for complete search history.

(56) References Cited

U.S. PATENT DOCUMENTS

| | | |
|---|---|---|
| 5,532,380 A | 7/1996 | Suzuki et al. |
| 6,333,332 B1 | 12/2001 | Han et al. |
| 6,462,093 B1 | 10/2002 | Miyamoto et al. |

FOREIGN PATENT DOCUMENTS

| | | | |
|---|---|---|---|
| EP | 1 930 003 A1 | | 6/2008 |
| JP | 63-130536 | | 6/1988 |
| JP | 3-223258 | | 10/1991 |
| JP | 9-77667 | | 3/1997 |
| JP | 11-286453 | | 10/1999 |
| JP | 2003-321459 | | 11/2003 |
| JP | 2004 359548 | | 12/2004 |
| JP | 2005-27515 | | 2/2005 |
| JP | 2007-091674 | * | 4/2007 |
| JP | 2007 91674 | | 4/2007 |
| JP | 2007-106736 | * | 4/2007 |
| JP | 2007 106736 | | 4/2007 |
| WO | WO 90/08557 A1 | | 8/1990 |
| WO | WO 94/14778 | | 7/1994 |
| WO | WO 97/06781 | | 2/1997 |

OTHER PUBLICATIONS

U.S. Appl. No. 12/523,067, filed Jul. 14, 2009, Murakami, et al.
Lian-Kaun Chen, et al., "Nitrofurantoin Solubility in Aqueous Urea and Creatinine Solution", Journal of Pharmaceutical Sciences, XP002590041, vol. 65, No. 6, 1976 pp. 868-872.
Suplementary European Search Report issued Oct. 27, 2010, in European Patent Application EP 08 75 1561.5-2123.
Iyakuhin Tenkabutsu Jiten, 1st edition, Yakuji Nippo Ltd. pp. 45-46, Creatinine, (Jan. 14, 1994) (with partial English translation).
U.S. Appl. No. 13/362,545, filed Jan. 31, 2012, Murakami, et al.
U.S. Appl. No. 13/362,527, filed Jan. 31, 2012, Murakami, et al.
U.S. Appl. No. 13/365,723, filed Feb. 3, 2012, Murakami, et al.
U.S. Appl. No. 13/365,785, filed Feb. 3, 2012, Murakami, et al.

* cited by examiner

*Primary Examiner* — Brandon Fetterolf
*Assistant Examiner* — Shirley V Gembeh
(74) *Attorney, Agent, or Firm* — Oblon, Spivak, McClelland, Maier & Neustadt, L.L.P.

(57) ABSTRACT

To provide a pharmaceutical composition containing a 2-nitroimidazole derivative, which has high solubility in an aqueous carrier and high stability.

The pharmaceutical composition is characterized by containing 1-(1-hydroxymethyl-2,3-dihydroxypropyl)oxymethyl-2-nitroimidazole and creatinine, and containing creatinine of 0.001 to 1 part by mass with respect to 1 part by mass of 1-(1-hydroxymethyl-2,3-dihydroxypropyl)oxymethyl-2-nitroimidazole.

10 Claims, 2 Drawing Sheets

PHARMACEUTICAL COMPOSITION

CROSS-REFERENCE TO RELATED APPLICATIONS

The present application is a 371 of PCT/JP08/000994 filed Apr. 16, 2008 and claims the benefit of JP 2007-156980 filed Jun. 14, 2007.

TECHNICAL FIELD

The present invention relates to a pharmaceutical composition and, more particularly, to a pharmaceutical composition suitable as a radiation-sensitizer in the form of injection solution.

BACKGROUND ART

In cancer radiotherapy, 2-nitroimidazole derivatives are known to be useful drugs as radiation-sensitizers for increasing radiation sensitivity of hypoxic cancer cells with radioresistance.

Among these 2-nitroimidazole derivatives, 1-(1-hydroxymethyl-2,3-dihydroxypropyl)oxymethyl-2-nitroimidazole, which is represented by the following formula (1):

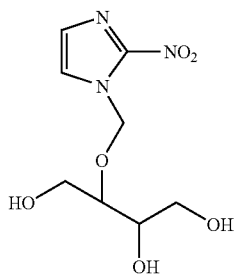

(hereinafter may be referred to as compound (1)), has particularly high hydrophilicity and virtually no transferability to neurocytes, to thereby serve as a radiation sensitizer having no toxicity to the central nervous system (see Patent Documents 2 and 3).

In addition to exhibiting radiation sensitizing effect on hypoxic cells, these compounds (1) have hydroxyl-group-removing action in nucleic acid (see Patent Document 4), apoptosis-signal maintaining action (see Patent Document 5), etc. Thus, the compounds (1) are considered to be useful drugs in cancer therapy.

Compound (1) has two asymmetric carbon atoms, and four stereoisomers: RR form, SS form, SR form, and RS form. Among these isomers, at present, clinical application is studied on only a racemic mixture of SR form and RS form.

All species of compound (1) have characteristics including high crystallinity, both water-solubility and lipid-solubility, and high tumor-affinity. These characteristics are thought to be attributed to an acyclic sugar nucleoside-like structure.

However, since compound (1) has high crystallinity and amphipathic nature, the crystal structure thereof must be broken in order to dissolve it in an aqueous carrier. This process requires heating and shaking for a long period of time. Therefore, long-term preparation must be performed before radiation, which problematically impairs operability. Such operation may affect the stability of the produced drug formulation.

Furthermore, the stability of a solution of compound (1) in aqueous carrier is readily lost at room temperature or higher.

Thus, the solution must be stored at low temperature (e.g., 5° C.), and storage at low temperature makes dissolution of compound (1) more difficult, which is also problematic.

In addition, when a lyophilized formulation of compound (1) is employed, a small amount of water considerably affects the stability of the drug formulation.

Meanwhile, creatinine is known to be an optional ingredient of a pharmaceutical composition. For example, a compound which is less soluble in water forms a solid solution with creatinine, to thereby convert the crystal form to an amorphous form, whereby dispersion and dissolution of the compound in water are promoted (Patent Document 6). However, creatinine has never been known to exhibit a direct effect on solubility of a compound.

Patent Document 1: JP-A-1991-223258
Patent Document 2: WO 1994/014778
Patent Document 3: JP-A-2003-321459
Patent Document 4: JP-A-2005-27515
Patent Document 5: JP-A-1997-77667
Patent Document 6: WO 1997/06781

DISCLOSURE OF THE INVENTION

Problems to be Solved by the Invention

An object of the present invention is to provide a pharmaceutical composition containing compound (1), wherein the composition has high solubility in an aqueous carrier and high stability.

Means for Solving the Problems

The present inventors have carried out extensive studies in order to enhance solubility and stability of compound (1), and have found that a pharmaceutical composition having high solubility in an aqueous carrier and high stability can be produced through adding, to compound (1), creatinine in an amount of 0.001 to 1 part by mass with respect to 1 part by mass of compound (1). The inventors have also found that the pharmaceutical composition exhibits excellent radiation sensitizing effect. The present invention has been accomplished on the basis of these findings.

Accordingly, the present invention provides the following.

(1) A pharmaceutical composition comprising 1-(1-hydroxymethyl-2,3-dihydroxypropyl)oxymethyl-2-nitroimidazole, which is represented by formula (1):

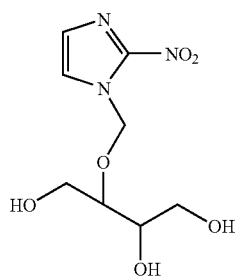

and creatinine in an amount of 0.001 to 1 part by mass with respect to 1 part by mass of compound (1).

(2) A pharmaceutical composition as described in (1), wherein the compound represented by formula (1) is an RS.SR racemic mixture of an isomer having a stereo-structure represented by formula (2):

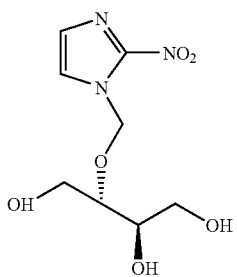

(2)

and an isomer having a stereo-structure represented by formula (3):

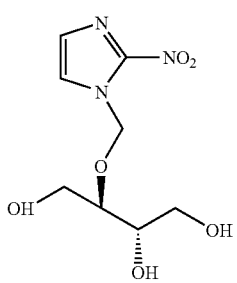

(3)

(3) A pharmaceutical composition as described in (1) or (2), which is in the form of injection.

(4) A pharmaceutical composition as described in any one of (1) to (3), which is a solution having a concentration of the compound represented by formula (1) of 5 to 10 mass %.

Effects of the Invention

The present invention can provide means for enhancing solubility and stability of an injection formulation of compound (1). In addition, the pharmaceutical composition of the present invention is particularly useful as a radiation-sensitizer.

BEST MODES FOR CARRYING OUT THE INVENTION

Figure 1:
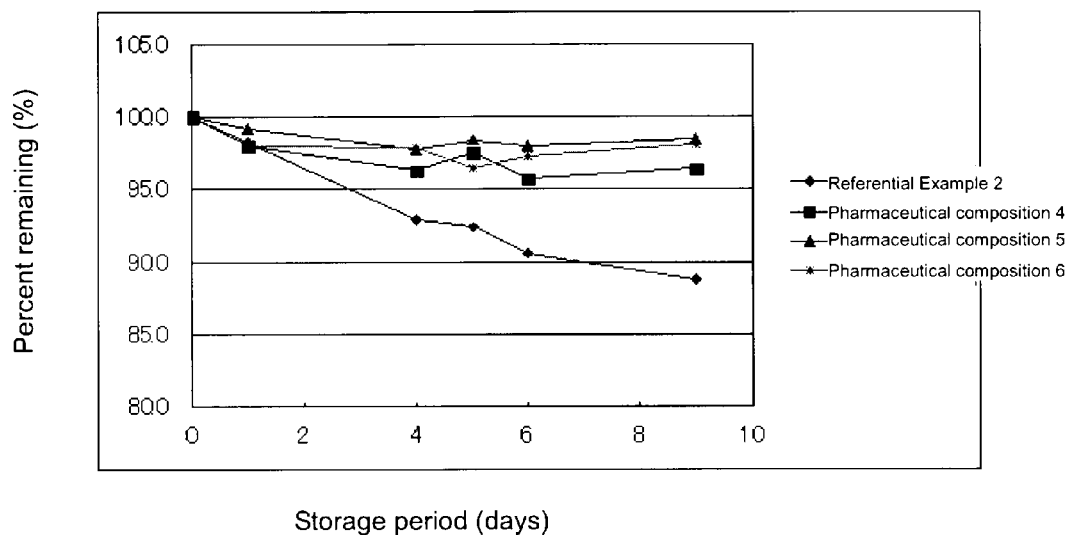
[FIG. 1] A graph showing stability of pharmaceutical compositions of the present invention.

The pharmaceutical composition of the present invention contains compound (1) as an essential ingredient. Compound (1) includes four stereoisomers: RS form, SR form, RR form, and SS form. In the pharmaceutical composition of the present invention, each of the optically active substances or a mixture thereof such as a racemic mixture of species of the optically active substances may be used. From the viewpoint of radiation sensitizing effect, preferred is an RS.SR racemic mixture of an isomer having a stereo-structure represented by formula (2) and an isomer having a stereo-structure represented by formula (3).

Compound (1) may be produced through a method disclosed in Patent Document 1 or 2. In one specific production procedure, 2-nitro-1-trimethylsilylimidazole is condensed with 2-acetoxymethoxy-1,3,4-triacetoxybutane in the presence of a Lewis acid, followed by deacetylation through reaction with sodium methoxide or a similar substance. In this case, stereo-characteristics of 2-acetoxymethoxy-1,3,4-triacetoxybutane are maintained in compound (1), the final product.

In the pharmaceutical composition of the present invention, the amount of compound (1) contained in the pharmaceutical composition is preferably 3 to 10 mass %, more preferably 4 to 8 mass %, still more preferably 5 to 8 mass %. When the amount is less than the lower limit, radiation sensitizing effect is unsatisfactory, whereas when the amount is in excess of the upper limit, radiation sensitizing effect and solubility are not satisfactory.

In the pharmaceutical composition of the present invention, the typical unit dose of compound (1) is, for example, 1 to 10 g for a male adult.

A characteristic feature of the pharmaceutical composition of the present invention resides in that the composition contains creatinine as an essential ingredient. The amount of creatinine contained in the composition is 0.001 to 1 part by mass with respect to 1 part by mass of compound (1), preferably 0.002 to 0.1 parts by mass, more preferably 0.004 to 0.04 parts by mass. In the presence of a vehicle such as water or physiological saline, creatinine can enhance solubility of compound (1) in the vehicle, leading to dissolution of compound (1) within a short period of time. Thus, the heating time required for solublilization or other process times can be shortened, whereby compound (1) in drug formulations can be maintained in a stable state.

The amount of creatinine with respect to the entire amount of the drug formulation is preferably 0.005 to 5 mass %, particularly preferably 0.01 to 1 mass %. When the amount is less than the lower limit, the effect of stability enhancement may fail to be attained, whereas when the amount is excessive, handling of the drug formulation upon administration may be difficult.

The pharmaceutical composition of the present invention, containing the aforementioned essential ingredients, is preferably employed for the purpose of cancer therapy, inter alia, enhancing radiation sensitivity of hypoxic cancer cells in cancer radiotherapy. Examples of the cancer to be preferably treated by the pharmaceutical composition include lung cancer and pancreatic cancer.

The drug formulation may be any drug formulations such as a peroral formulation and an injection formulation. Among them, an injection formulation is preferred from the viewpoint of rapid metabolism. The injection formulation is preferably dripping formulation for the following reason. The dose of a formulation containing compound (1), serving as an effective ingredient, is increased, since a large amount of the effective ingredient must be administered. In this case, a single dose administration may cause a risky state of the relevant patient. No particular limitation is imposed on the form of such an injection formulation, and it may be a solution or a freeze-dry formulation. However, a solution is preferred, since a satisfactory solubility can be attained.

No particular limitation is imposed on the vehicle employed in the solution include, so long as it is an aqueous carrier. Examples of preferred vehicles include pure water, physiological saline, and glucose solution which may be isotonified.

In addition to the aforementioned essential ingredients, the pharmaceutical composition of the present invention may optionally contain any of the formulation ingredients generally employed in preparation of drugs, so long as the effect of the present invention is not impaired.

Examples of such optional ingredients include polyhydroxylic alcohols such as Macrogol; tonicity agents such as sodium chloride; buffers such as phosphate; excipients such as crystalline cellulose and starch; nonionic surfactants such as polyoxyethylene-hardened castor oil; anionic surfactants such as sodium lauryl sulfate; viscosity-increasing polysaccharides such as gum arabic; lubricants such as magnesium stearate; colorants; flavoring agents/deodorants; binders such as hydroxypropyl cellulose; and coating agents such as "Eudragit" (registered trademark). When the pharmaceutical composition is an injection liquid, a particularly preferred formulation contains only the essential ingredients and a vehicle and does not contain other ingredients.

The pharmaceutical composition of the present invention may be produced through processing the aforementioned essential ingredients and optional ingredients in a routine manner.

EXAMPLES

The present invention will next be described in more detail by way of Examples, which should not be construed as limiting the invention thereto.

Example 1

Injection solutions for drip infusions, which are the pharmaceutical composition of the present invention, were prepared according to the below-described formulations. Specifically, the formulated ingredients were stirred at 30° C. for dissolution. In each case, the time required for dissolution was measured. The results are shown in Table 2. As is clear from Table 2, the pharmaceutical composition of the present invention has been found to provide enhanced solubility of 1-(1-hydroxymethyl-2,3-dihydroxypropyl)oxymethyl-2-nitroimidazole (compound 1). Note that a sample of Referential Example 1 contained no creatinine.

TABLE 1

| Ingredient | |
|---|---|
| Compound (1) | 6 g |
| Creatinine | amount shown in Table 2 |
| Water | to total volume of 100 mL |

TABLE 2

| Samples | Mass of creatinine (g) | Time required for dissolution (min) |
|---|---|---|
| Pharmaceutical compn. 1 | 0.05 | 25 |
| Pharmaceutical compn. 2 | 0.1 | 25 |
| Pharmaceutical compn. 3 | 0.2 | 20 |
| Ref. Ex. 1 | 0 | 30 |

When these samples were allowed to stand at 20° C., no change was observed within five hours from start of storage. However, 22 hours after the start of storage, precipitation was observed. The amount of precipitation was the largest in the case of Referential Example 1, and decreased in the order of the cases of pharmaceutical composition 1, pharmaceutical composition 2, and pharmaceutical composition 3.

Example 2

In a manner similar to Example 1, injection solutions for drip infusion (i.e., pharmaceutical compositions 4 to 6), which are pharmaceutical compositions of the present invention, were prepared according to the below-described formulations.

TABLE 3

| Ingredient | |
|---|---|
| Compound (1) | 5 g |
| Creatinine | amount shown in Table 4 |
| Water | to total volume of 100 mL |

TABLE 4

| Samples | Mass of creatinine (g) |
|---|---|
| Pharmaceutical compn. 4 | 0.02 |
| Pharmaceutical compn. 5 | 0.1 |
| Pharmaceutical compn. 6 | 0.2 |
| Ref. Ex. 2 | 0 |

Example 3

<Test Example 1>

Each of the above-produced pharmaceutical compositions 4 to 6 and the composition of Reference Example 2 was stored under severe conditions (55° C.) for 9 days, and the compound (1) content of the composition was determined through HPLC. The determined value was divided by 5, followed by multiplication by 100, to thereby obtain percent content (%). The results are shown in FIG. 1. As shown in FIG. 1, the pharmaceutical compositions of the present invention exhibited excellent stability. HPLC was carried out under the following conditions: ODS column (4.6 mm×250 mm), column temperature (40° C.), flow rate 1 mL/min, mobile phase (1% aqueous methanol), and detection UV region (320 nm).

Example 4

According to the below-described formulation, a drug solution was prepared, and a vial was filled with the solution in an antiseptic state. The solution was lyophilized, to thereby produce amorphous lyophilized formulation for injection containing microcrystals (i.e., pharmaceutical composition 7 of the present invention).

TABLE 5

| Ingredient | |
|---|---|
| Compound (1) | 5 g |
| Creatinine | 0.2 g |
| Water | to total volume of 100 mL |

Example 5

<Test Example 2>

Figure 2:
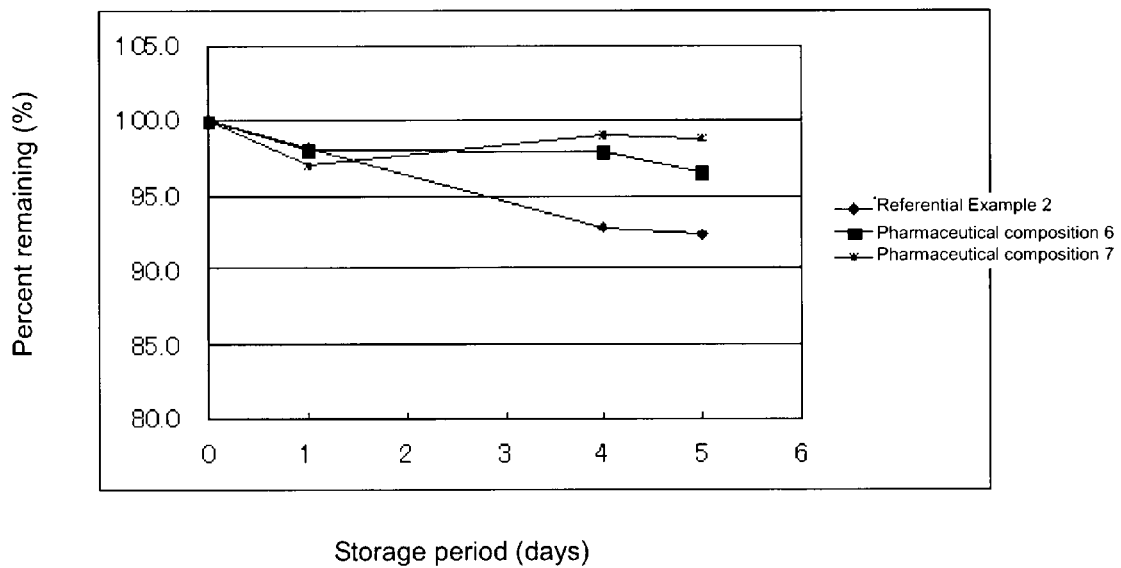
[FIG. 2] A graph showing stability of pharmaceutical compositions of the present invention.

The pharmaceutical compositions 6 and 7, and the composition of Referential Example 2 were stored at 55° C. for 5 days, and the percent compound (1) content of each composition was determined in a manner similar to that of Example 3. FIG. 2 shows the results. As shown in FIG. 2, stability enhance effect was confirmed in the lyophilized drug formulation.

Example 6

<Test Example 3>

Figure 3:
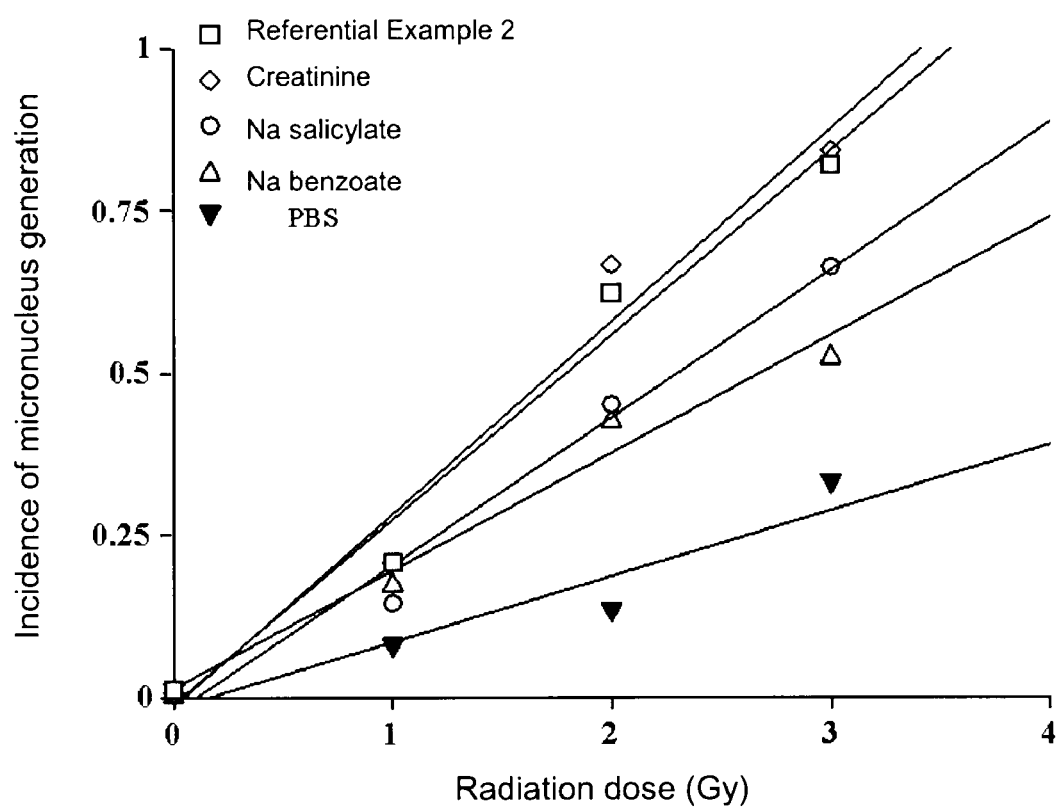
[FIG. 3] A graph showing the radiation sensitizing effect of the pharmaceutical composition of the present invention.

The radiation sensitizing effect of the invention was investigated through the micronucleus method by use of mouse squamous cell carcinoma cells (SCCVII). Specifically, a gas (95% $N_2$+5% $CO_2$) was caused to pass through mouse squamous cell carcinoma cells (SCCVII) for 20 minutes, to thereby render the cells in a hypoxic state. Subsequently, in the presence of PBS and a test pharmaceutical formulation, the cells were irradiated with X-rays (0, 1, 2, or 3 Gy). The following tested pharmaceutical formulations were employed: Referential Example 2 (employed in Example 2), pharmaceutical composition 6, composition of Comparative Example 1 (prepared from pharmaceutical composition 6 by use of sodium salicylate instead of creatinine), and composition of Comparative Example 2 (prepared from pharmaceutical composition 6 by use of sodium benzoate instead of creatinine). After irradiation, the cells were washed and cultured for about 24 hours in the presence of cytochalasin B, to thereby generate binucleate cells. The thus-treated cells were fixed and fluoro-stained, and the number of binucleate cells and that of micronuclei were counted, whereby incidence of micronucleus generation was determined. FIG. 3 shows the results.

In FIG. 3, "creatinine" indicates pharmaceutical composition 6, "sodium salicylate" indicates Comparative Example 1, and "sodium benzoate" indicates Comparative Example 2. In non-irradiated groups, incidence of micronucleus generation was not affected by PBS or any of the tested formulations. No direct effect of the formulations on the cells was observed. In other words, direct toxicity to the cells by the additives including creatinine was not observed. In contrast, in irradiated groups, all tested formulations exhibited radiation sensitizing effect on cells in a hypoxic state. In particular, only pharmaceutical composition 6 of the present invention did not vary the sensitizing effect, as compared with Reference Example 2 containing no additives.

Industrial Applicability

The present invention can be applied to pharmaceutical and other medical Fields.

The invention claimed is:

1. A pharmaceutical composition comprising 1-(1-hydroxymethyl-2,3-dihydroxypropyl)oxymethyl-2-nitroimidazole, which is represented by formula (1):

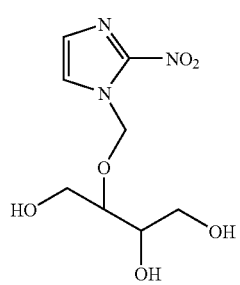

(1)

and creatinine in an amount of 0.001 to 1 part by mass with respect to 1 part by mass of compound (1).

2. The pharmaceutical composition according to claim 1, which is in the form of injection.

3. The pharmaceutical composition according to claim 1, which is a solution having a concentration of the compound represented by formula (1) of 5 to 10 mass %.

4. The pharmaceutical composition according to claim 2, which is a solution having a concentration of the compound represented by formula (1) of 5 to 10 mass %.

5. The pharmaceutical composition according to claim 1, wherein the compound represented by formula (1) is in a RS form, a SS form, a SR form, a RS form, or a combination thereof.

6. The pharmaceutical composition according to claim 5, wherein the compound represented by formula (1) is an RS.SR racemic mixture of an isomer having a stereo-structure represented by formula (2):

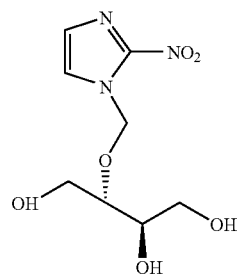

(2)

and an isomer having a stereo-structure represented by formula (3):

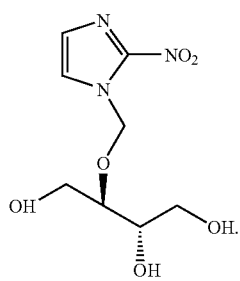

(3)

7. The pharmaceutical composition according to claim 6, which is in the form of injection.

8. The pharmaceutical composition according to claim 6, which is a solution having a concentration of the compound represented by formula (1) of 5 to 10 mass %.

9. The pharmaceutical composition according to claim 5, which is in the form of injection.

10. The pharmaceutical composition according to claim 5, which is a solution having a concentration of the compound represented by formula (1) of 5 to 10 mass %.

* * * * *